(12) United States Patent
Inman et al.

(10) Patent No.: US 9,080,968 B2
(45) Date of Patent: Jul. 14, 2015

(54) METHODS AND SYSTEMS FOR POINT OF USE REMOVAL OF SACRIFICIAL MATERIAL

(71) Applicant: LIFE TECHNOLOGIES CORPORATION, Carlsbad, CA (US)

(72) Inventors: Christina Inman, San Mateo, CA (US); Alexander Mastroianni, Alameda, CA (US); Wolfgang Hinz, New Haven, CT (US); Shifeng Li, Fremont, CA (US); Scott Benson, Alameda, CA (US)

(73) Assignee: Life Technologies Corporation, Carlsbad, CA (US)

( * ) Notice: Subject to any disclaimer, the term of this patent is extended or adjusted under 35 U.S.C. 154(b) by 35 days.

(21) Appl. No.: 13/734,696

(22) Filed: Jan. 4, 2013

(65) Prior Publication Data

US 2014/0191292 A1    Jul. 10, 2014

(51) Int. Cl.
*H01L 27/14* (2006.01)
*G01N 27/414* (2006.01)

(52) U.S. Cl.
CPC .................................. *G01N 27/4145* (2013.01)

(58) Field of Classification Search
CPC ....................... H01L 27/4148; H01L 29/66007
USPC .......................................... 257/253, E29.166
See application file for complete search history.

(56) References Cited

U.S. PATENT DOCUMENTS

| | | | |
|---|---|---|---|
| 4,086,642 A | 4/1978 | Yoshida et al. | |
| 4,411,741 A | 10/1983 | Janata | |
| 4,490,678 A | 12/1984 | Kuisl et al. | |
| 4,641,084 A | 2/1987 | Komatsu | |
| 4,701,253 A | 10/1987 | Litenberg et al. | |
| 4,722,830 A | 2/1988 | Urie et al. | |
| 4,743,954 A | 5/1988 | Brown | |
| 4,764,797 A | 8/1988 | Shaw et al. | |
| 4,777,019 A | 10/1988 | Dandekar | |

(Continued)

FOREIGN PATENT DOCUMENTS

| | | |
|---|---|---|
| CN | 1582334 | 2/2005 |
| CN | 1585896 | 2/2005 |

(Continued)

OTHER PUBLICATIONS

Bockelmann, U. et al., "Detecting DNA by field effect transistor arrays", *Proceedings of the 2006 IFIP International Conference on Very Large Scale Integration*, 2006, 164-168.

(Continued)

*Primary Examiner* — Chandra Chaudhari

(57) ABSTRACT

A method of manufacturing a sensor, the method including forming an array of chemically-sensitive field effect transistors (chemFETs), depositing a dielectric layer over the chemFETs in the array, depositing a protective layer over the dielectric layer, etching the dielectric layer and the protective layer to form cavities corresponding to sensing surfaces of the chemFETs, and removing the protective layer. The method further includes, etching the dielectric layer and the protective layer together to form cavities corresponding to sensing surfaces of the chemFETs. The protective layer is at least one of a polymer, photoresist material, noble metal, copper oxide, and zinc oxide. The protective layer is removed using at least one of sodium hydroxide, organic solvent, aqua regia, ammonium carbonate, hydrochloric acid, acetic acid, and phosphoric acid.

7 Claims, 6 Drawing Sheets

(56) References Cited

U.S. PATENT DOCUMENTS

| | | |
|---|---|---|
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,682,936 B2 | 1/2004 | Kovacs |
| 6,686,638 B2 * | 2/2004 | Fischer et al. ............... 257/414 |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,888,194 B2 | 5/2005 | Yoshino |
| 6,906,524 B2 | 6/2005 | Chung et al. |
| 6,919,211 B1 | 7/2005 | Fodor et al. |
| 6,926,865 B2 | 8/2005 | Howard |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,022,288 B1 | 4/2006 | Boss |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,361,946 B2 * | 4/2008 | Johnson et al. ............... 257/253 |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,455,971 B2 | 11/2008 | Chee et al. |
| 7,462,512 B2 * | 12/2008 | Levon et al. ................. 257/414 |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,515,124 B2 | 4/2009 | Yaguma et al. |
| 7,575,865 B2 | 8/2009 | Leamon et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,303 B1 | 10/2009 | Lee |
| 7,612,817 B2 | 11/2009 | Tay |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,785,790 B1 | 8/2010 | Church et al. |
| 7,859,029 B2 | 12/2010 | Lee et al. |
| 7,885,490 B2 | 2/2011 | Heideman et al. |
| 7,888,013 B2 | 2/2011 | Miyahara et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,960,776 B2 | 6/2011 | Kim et al. |
| 8,067,731 B2 | 11/2011 | Matyjaszczyk et al. |
| 8,124,936 B1 | 2/2012 | Lagna |
| 8,199,859 B2 | 6/2012 | Zerbe et al. |

(56) References Cited

U.S. PATENT DOCUMENTS

| | | |
|---|---|---|
| 8,217,433 B1 | 7/2012 | Fife |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,343,856 B2 | 1/2013 | Therrien et al. |
| 8,426,898 B2 | 4/2013 | Rothberg et al. |
| 8,552,771 B1 | 10/2013 | Jordan et al. |
| 8,558,288 B2 | 10/2013 | Rothberg et al. |
| 8,592,154 B2 | 11/2013 | Rearick |
| 8,673,627 B2 | 3/2014 | Nobile et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0150909 A1 | 10/2002 | Stuelpnagel et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 | 3/2003 | Matson |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0138809 A1 | 7/2003 | Williams et al. |
| 2003/0148301 A1 | 8/2003 | Aono et al. |
| 2003/0148344 A1 | 8/2003 | Rothberg et al. |
| 2003/0155942 A1 | 8/2003 | Thewes et al. |
| 2003/0157504 A1 | 8/2003 | Chee et al. |
| 2003/0186262 A1 | 10/2003 | Cailloux et al. |
| 2003/0194740 A1 | 10/2003 | Williams |
| 2003/0215857 A1 | 11/2003 | Kilger et al. |
| 2003/0224419 A1 | 12/2003 | Corcoran et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0079636 A1 | 4/2004 | Hsia et al. |
| 2004/0106211 A1 | 6/2004 | Kauer et al. |
| 2004/0134798 A1 | 7/2004 | Toumazou et al. |
| 2004/0136866 A1 | 7/2004 | Pontis et al. |
| 2004/0185484 A1 | 9/2004 | Costa et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0202582 A1 | 9/2005 | Eversmann et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2006/0000772 A1 | 1/2006 | Sano et al. |
| 2006/0016699 A1 | 1/2006 | Kamahori et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0231824 A1 | 10/2007 | Chee et al. |
| 2007/0233477 A1 | 10/2007 | Halowani et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |

(56) References Cited

U.S. PATENT DOCUMENTS

| | | |
|---|---|---|
| 2008/0032295 A1 | 2/2008 | Toumazou et al. |
| 2008/0035494 A1 | 2/2008 | Gomez et al. |
| 2008/0094074 A1 | 4/2008 | Kim et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0185616 A1 | 8/2008 | Johnson et al. |
| 2008/0186093 A1 | 8/2008 | Forbes |
| 2008/0197022 A1 | 8/2008 | Suzuki et al. |
| 2008/0205559 A1 | 8/2008 | Iida |
| 2008/0210931 A1 | 9/2008 | Truong et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286767 A1 | 11/2008 | Miyahara et al. |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0120905 A1 | 5/2009 | Kohl et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0244106 A1 | 9/2010 | Parker et al. |
| 2010/0255595 A1 | 10/2010 | Toumazou et al. |
| 2010/0273166 A1 | 10/2010 | Garcia |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife et al. |
| 2012/0074956 A1 | 3/2012 | Fife et al. |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0161207 A1 | 6/2012 | Homyk et al. |
| 2012/0168307 A1 | 7/2012 | Fife |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| CN | 1826525 | 8/2006 |
| CN | 102203282 | 9/2011 |
| DE | 102008012899 | 9/2009 |
| EP | 0223618 | 5/1987 |
| EP | 1371974 | 12/2003 |
| EP | 1432818 | 6/2004 |
| EP | 1542009 | 6/2005 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 2005218310 | 8/2004 |
| JP | 05077210 | 3/2005 |
| JP | 05518541 | 6/2005 |
| JP | 2005518541 | 6/2005 |
| JP | 06138846 | 6/2006 |
| JP | 2002272463 | 9/2009 |
| JP | 2011525810 | 9/2011 |
| KR | 100442838 | 7/2004 |
| KR | 100455283 | 10/2004 |
| WO | 89/09283 | 10/1989 |
| WO | 98/13523 | 4/1998 |
| WO | 98/46797 | 10/1998 |
| WO | 01/20039 | 3/2001 |
| WO | 01/42498 | 6/2001 |
| WO | 01/81896 | 11/2001 |
| WO | 02/077287 | 10/2002 |
| WO | 02/086162 | 10/2002 |
| WO | 03/073088 | 9/2003 |
| WO | 2004/040291 | 5/2004 |
| WO | WO2004040291 | 5/2004 |
| WO | WO2004048962 | 6/2004 |
| WO | WO2005015156 | 2/2005 |
| WO | 2005/047878 | 5/2005 |
| WO | WO2005043160 | 5/2005 |
| WO | 2005/054431 | 6/2005 |
| WO | 2005/084367 | 9/2005 |
| WO | WO2005090961 | 9/2005 |

(56) References Cited

FOREIGN PATENT DOCUMENTS

| WO | 2006/005967 | 1/2006 |
| WO | 2006/022370 | 3/2006 |
| WO | 2007/086935 | 8/2007 |
| WO | 2008007716 | 1/2008 |
| WO | 2008/058282 | 5/2008 |
| WO | 2008/076406 | 6/2008 |
| WO | 2008/107014 | 9/2008 |
| WO | 2009/012112 | 1/2009 |
| WO | WO2009041917 | 4/2009 |
| WO | WO2009081890 | 7/2009 |
| WO | 2009/158006 | 12/2009 |
| WO | 2010/008480 | 1/2010 |
| WO | 2010/047804 | 4/2010 |
| WO | 2010/138182 | 12/2010 |
| WO | 2010/138188 | 12/2010 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/006222 | 1/2012 |

OTHER PUBLICATIONS

EP13177590.0 EP Search Report Nov. 20, 2013.
EP13177039.8 EP Search Report Nov. 21, 2013.
EP13174555.6 EP Search Report Nov. 21, 2013.
EP13174555.6 EP Extended Search Report Dec. 12, 2013.
EP11801439.8 EP Extended Search Report dated Mar. 7, 2014.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Tokuda, T. et al., "A CMOS image sensor with optical and potential dual imaging function for on-chip bioscientific applications", *Sensors and Actuators A*, vol. 125, No. 2, 2006, 273-280.
Wood, et al. "Base composition-independent hybridization in tetramethylammonium chloride: a method for oligonucleotide screening of highly complex gene libraries" Proc. Nat. Acad. Sci., 1985, pp. 1585-1588.
EP14152861.2 EP Search Report date Jul. 7, 2014.
Palan, B. et al., "New ISFET sensor interface circuit for biomedical applications", Sensors and Actuators B: Chemical: International Journal Devoted to Research and Development of Physical and Chemical Transducers, Elsevier S.A. Ch., vol. 57, No. 1-3, 1999, pp. 63-68.
PCT/US2013/022129 International Preliminary Report on Patentability dated Jul. 22, 2014.
PCT/US2013/022140 International Preliminary Report on Patentability dated Jul. 22, 2014.
Zhao, B. et al., "Floating-Gate Ion Sensitive Field-Effect Transistor for Chemical and Biological Sensing", MRS Proceedings, vol. 828, 2004, pp. 349-354.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chinese Patent Application 200780051353.2 Second Office Action Mailed Mar. 5, 2013.
Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP11801437.2 Extended European Search Report dated Jul. 25, 2013.

EP11804218.3 Extended European Search Report dated Jul. 11, 2013.
EP11804218.3 First Office Action dated Jul. 29, 2013.
EP11827128.7 European Search Report dated Aug. 1, 2013.
EP13163995.7 Extended European Search Report dated Aug. 20, 2013.
Eriksson, J. et al. "Pyrosequencing Technology at Elevated Temperature" Electrophoresis, vol. 25, 2004, pp. 20-27.
Hizawa, et al. "Sensing Characteristics of Charge Transfer Type pH Sensor by Accumulative Operation" IEEE Sensors, EXCO, Daegu, Korea, 2006, pp. 144-147.
Krause, M. et al., "Extended Gate Electrode Arrays for Extracellular Signal Recordings" Sensors and Actuators B, vol. 70, 2000, pp. 101-107.
Lee, S. et al. "An Enhanced Glucose Biosensor Using Charge Transfer Techniques" Biosensors and Bioelectronics, vol. 24, 2008, pp. 650-656.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-2255.
Milgrew, M.J. et al., "The Development of Scalable Sensor Arrays Using Standard CMOS Technology" ScienceDirect, Sensors and Actuators, vol. 103, 2004, pp. 37-42.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
PCT/US2010/048835 International Preliminary Report on Patentability Mailed Mar. 19, 2013.
PCT/US2011/042668 International Preliminary Report on Patentability Mailed Mar. 26, 2013.
PCT/US2011/042683 International Preliminary Report on Patentability Mailed Jun. 4, 2013.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.
Pollack, J. et al. "Genome-Wide Analysis of DNA copy-number changes using cDNA Microarrays", Nature Genetics, vol. 23, 1999, pp. 41-46.
Premanode, B. et al. "Drift Reduction in Ion-Sensitive FETs Using Correlated Double Sampling", Electronics Letters, IEEE Stevenage, GB, vol. 43 (16) Aug. 2, 2007.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
[No Author Listed], "ISFET Wikipedia article", *Wikipedia*, Last modified Nov. 7, 2006.
Ahmadian, A. et al., "Single-nucleotide polymorphism analysis by pyrosequencing", *Anal. Biochem*, vol. 280, 2000, pp. 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767 Search Information Statement Mailed Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.

(56) References Cited

OTHER PUBLICATIONS

Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.

Barbaro, M. et al., "Fully electronic DNA hybridization detection by a standard CMOS biochip", *Sensors and Actuators B Chemical*, vol. 118, 2006, pp. 41-46.

Bashford, G. et al., "Automated bead-trapping apparatus and control system for single-molecule DNA sequencing", *Optics Express*, vol. 16(5), Mar. 3, 2008, pp. 3445-3455.

Baumann, W. et al., "Microelectronic sensor system for microphysiological application on living cells", *Sensors Actuators B*, vol. 55, 1999, pp. 77-89.

Bausells, J. et al., "Ion-sensitive field-effect transistors fabricated in a commercial CMOS technology", *Sensors and Actuators B Chemical*, vol. 57, 1999, pp. 56-62.

Bergveld, P., "ISFET, 2003, Theory and Practice", *IEEE Sensor Conference*, Toronto, Oct. 2003, 2003, pp. 1-26.

Bergveld, P., "Thirty years of ISFETOLOGY What happened in the past 30 years and what may happen in the next 30 years", *Sensors and Actuators B*, vol. 88, 2003, pp. 1-20.

Besselink, G et al., "ISFET Affinity Sensor", *Methods in Biotechnology, vol. 7: Affinity Biosensors: Techniques and Protocols*, 1998, pp. 173-185.

Bobrov, P. et al., "Chemical sensitivity of an ISFET with Ta2O5 membrane in strong acid and alkaline solutions", *Sensors and Actuators B*, vol. 3, 1991, pp. 75-81.

Bousse, L. et al., "A process for the combined fabrication of ion sensors and CMOS circuits", *IEEE Electron Device Letters*, vol. 9(1), 1988, pp. 44-46.

Bousse, L. et al., "Zeta potential measurements of Ta2O5 and SiO2 thin films", *J. Colloid Interface Sci.*, vol. 147(1), 1991, pp. 22-32.

Chen, Y. et al., "Nanoscale field effect transistor for biomolecular signal amplification", *App Phys Letter*, vol. 91, 2007, pp. 243511-1-243511-3.

Chen, Y. et al., "Silicon-based nanoelectronic field-effect pH sensor with local gate control", *App Phys Letter*, vol. 89, 2006, pp. 223512-1-223512-3.

Chou, J. et al., "Letter to the Editor on Simulation of Ta2O5 gate ISFET temperature characteristics", *Sensors and Actuators B*, vol. 80, 2001, pp. 290-291.

Chou, J. et al., "Simulation of Ta2O5 gate ISFET temperature characteristics", *Sensor and Actuators B*, vol. 71, Letter to the Editor, 2000, pp. 73-76.

Chung, W-Y et al., "ISFET interface circuit embedded with noise rejection capability", *Electronics Letters*, vol. 40(18), e-pub; 2 pages, 2004.

Chung, W-Y et al., "ISFET performance enhancement by using the improved circuit techniques", *Sensors and Actuators B*, vol. 113, 2006, pp. 555-562.

Eijkel, J. et al., "Measuring Donnan-related phenomena using a solid-state ion sensor and a concentration-step method", *J. Membrane Sci.*, vol. 127, 1997, pp. 203-221.

Eijkel, J., "Potentiometric detection and characterization of adsorbed protein using stimulus-response measurement techniques", *Thesis*, Sep. 3, 1955, pp. 1-147; 160-192.

Eltoukhy, H et al., "A 0.18um CMOS 10-6 lux Bioluminescence Detection System-on-Chip", *ISSCC 2004/Session12/Biomicrosystems/12.3*, 2004, pp. 1-3.

Eltoukhy, H. et al., "A. 0.18-um CMOS Bioluminescence Detection Lab-on-Chip", *IEEE J Solid-State Circuits*, vol. 41(3), 2006, pp. 651-662.

EP7867780.4 Examination Report Mailed Jul. 3, 2012.

Eriksson, J. et al., "Pyrosequencing technology at elevated temperature", *Electrophoresis*, vol. 25, 2004, pp. 20-27

Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.

Eversmann, B. et al., "A 128×128 CMOS Biosensor Array for Extracellular Recording of Neural Activity", *IEEE J. Solid-State Circ.*, vol. 38(12), Dec. 12, 2003, pp. 2306-2317.

Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.

Finn, A et al., "Towards an Optimization of FET-Based Bio-Sensors", *European Cells and Materials*, vol. 4, Sup 2, 2002, pp. 21-23.

Fraden, J., "Handbook of Modern Sensors—Physics, Designs, and Applications . . .", *17.3.2 CHEMFET Sensors*, 1996, pp. 499-501.

Fritz, J. et al., "Electronic detection of DNA by its intrinsic molecular charge", *PNAS*, vol. 99(22), 2002, pp. 14142-14146.

GB0811656.8 Search and Examination Report Mailed Mar. 12, 2010.

GB0811656.8 Search Report Mailed Sep. 21, 2009.

GB0811657.6 Examination Report Mailed Jun. 30, 2010.

GB0811657.6 Search Report under Section 17 Mailed Oct. 26, 2009.

Gracia, I. et al., "Test Structures for ISFET Chemical Sensors", *Proc IEEE 1992 Intl Conf Microelec Test Struct*, vol. 5, 1992, pp. 156-159.

Hammond, P. et al., "A System-on-Chip Digital pH Meter for Use in a Wireless Diagnostic Capsule", *IEEE Transactons on Biomedical Engineering*, vol. 52(4), 2005, pp. 687-694.

Hammond, P. et al., "Design of a Single-Chip pH Sensor Using a Conventional 0.6-μm CMOS Process", *IEEE Sensors Journal*, vol. 4(6), 2004, pp. 706-712.

Hammond, P. et al., "Encapsulation of a liquid-sensing microchip using SU-8 photoresist", *MicroElectronic Engineering*, vol. 73-74, 2004, pp. 893-897.

Hammond, S. et al., "Genomic sequencing and analysis of a Chinese Hamster ovary cell line using Illumina sequencing technology", *BMC Genomics*, vol. 12:67, 2011, pp. 1-8.

Han, Y., "Label-free detection of biomolecules by a field-effect transistor microarray biosensor with bio-functionalized gate surfaces", *Masters Dissertation*, 2006, pp. 1-63.

Hara, H. et al., "Dynamic response of a Ta205-gate pH-sensitive field-effect transistor", *Sensors Actuators B*, vol. 32, 1996, pp. 115-119.

Hermon, Z. et al., "Miniaturized bio-electronic hybrid for chemical sensing applications", *Tech Connect News*, Apr. 22, 2008, pp. 1.

Hideshima, S. et al., "Detection of tumor marker in blood serum using antibody-modified field effect transistor with optimized BSA blocking", *Sensors and Actuations B: Chemical*, vol. 161, 2012, pp. 146-150.

Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.

Hizawa, T et al., "Fabrication of a two-dimensional pH image sensor using a charge transfer technieue", *Sensors and Actuators B Chemical*, vol. 117, 2006, pp. 509-515.

Hizawa, T. et al., "32×32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, 2007, pp. 1311-1312.

Jakobson, C. et al., "Low frequency noise and drift in Ion Sensitive Field Effect Transistors", *Sensors Actuators B*, vol. 68, 2000, pp. 134-139.

Ji, H. et al., "A CMOS contact imager for locating individual cells", *ISCAS*, 2006, pp. 3357-3360.

Ji, H. et al., "Contact Imaging: Simulation and Experiment", *IEEE Trans Circuits Systems—I: Regular Papers*, vol. 54(8), 2007, pp. 1698-1710.

Kim, D. et al., "An FET-type charger sensor for highly sensitive detection of DNA sequence", *Biosens Bioelectron*, vol. 20(1), 2004, pp. 69-74.

Klein, M., "Time effects of ion-sensitive field-effect transistors", *Sens Act B*, vol. 17, 1989.

Koch, S et al., "Protein detection with a novel ISFET-based zeta potential analyzer", *Biosensors & Bioelectronics*, vol. 14, 1999, pp. 413-421.

Kruise, J. et al., "Detection of protein concentrations using a pH-step titration method", *Sensors Actuators B*, vol. 44, 1997, pp. 297-303.

(56) References Cited

OTHER PUBLICATIONS

Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreator Chips", *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE Intl. Conf. on Microelectronic Test Structures*, vol. 9, 1996, pp. 123-128.
Margulies, M. et al., "Genome sequencing in microfabricated high-density picolitre reactors", *Nature*, vol. 437(7057), 2005, pp. 376-380.
Marshall, A. et al., "DNA chips: an array of possibilities", *Nature Biotechnology*, vol. 16, 1998, pp. 27-31.
Martinoia, S. et al., "A behavioral macromodel of the ISFET in SPICE", *Sensors Actuators B*, vol. 62, 2000, pp. 182-189.
Martinoia, S. et al., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), 2006, pp. 1037-1044.
Milgrew, M. et al., "A 16×16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "A large transistor based sensor array chip for direct extracellular imaging", *Sensors and Actuators B Chemical*, vol. 111-112, 2005, pp. 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B*, vol. 103, 2004, pp. 37-42.
Milgrew, M. et al., "The fabrication of scalable multi-sensor arrays using standard CMOS technology", *2003 IEEE Custom Integrated Circuits Conference*, 2003, pp. 513-516.
Miyahara, Y. et al., "Biochip Using Micromachining Technology", *J. Institute of Electrostatics, Japan*, vol. 27(6), 2003, pp. 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behavior of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.

Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), 2006, pp. 4261-4269.
PCT/JP2005/001987 International Search Report Mailed Apr. 5, 2005.
PCT/JP2005/015522 International Preliminary Report on Patentability Mailed Mar. 19, 2007.
PCT/JP2005/015522 International Search Report Mailed Sep. 27, 2005.
PCT/US/2009/05745 International Preliminary Report on Patentability Issued Apr. 26, 2011.
PCT/US/2009/05745 International Search Report Mailed Dec. 11, 2009.
PCT/US/2009/05745 Written Opinion Mailed Dec. 11, 2009.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011.
PCT/US2010/001543 International Search Report and Written Opinion Mailed Oct. 13, 2010.
PCT/US2010/001553 International Preliminary Report on Patentability Mailed Dec. 8, 2011.
PCT/US2010/001553 International Search Report Mailed Jul. 28, 2010.
PCT/US2010/001553 Written Opinion Mailed Jul. 14, 2010.
PCT/US2010/048835 International Search Report and Written Opinion Mailed Dec. 16, 2010.
PCT/US2011/042655 International Search Report Mailed Oct. 21, 2011.
PCT/US2011/042660 International Search Report Mailed Nov. 2, 2011.
PCT/US2011/042665 International Search Report Mailed Nov. 2, 2011.
PCT/US2011/042668 International Search Report Mailed Oct. 28, 2011.
PCT/US2011/042669 International Search Report Mailed Jan. 9, 2012.
PCT/US2011/042669 Written Opinion Mailed Jan. 9, 2012.
PCT/US2011/042683 International Search Report Mailed Feb. 16, 2012.
PCT/US2011/042683 Written Opinion Mailed Feb. 16, 2012.
Poghossian, A. et al., "Functional testing and characterization of ISFETs on wafer level by means of a micro-droplet cell", *Sensors*, vol. 6, 2006, pp. 397-404.
Pourmand, N et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), 2006, 2 pages.
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.

(56) References Cited

OTHER PUBLICATIONS

Purushothaman, S. et al., "Towards Fast Solid State DNA Proceedings", *IEEE ISCAS 2002 Proceedings*, Circuits and Systems, vol. 4, 2002, pp. IV-169-IV-172.
Rodriguez-Villegas, E., "Solution to trapped charge in FGMOS transistors", *Electronics Letters*, vol. 39(19), 2003.
Ronaghi, M. et al., "A Sequencing Method Based on Real-Time Pyrophosphate", *Science*, vol. 281, 1998, pp. 363-365.
Sakata, T. et al., "Cell-based field effect devices for cell adhesion analysis", *Intl. Conf. on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proc. of 2006 Intl. Conf. on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-117.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.
Sakata, T. et al., "Direct transduction of allele-specific primer extension into electrical signal using genetic field effect transistor", *Biosensors and Bioelectronics*, vol. 22, 2007, pp. 1311-1316.
Sakata, T. et al., "DNA Analysis Chip Based on Field-Effect Transistors", *Japanese Journal of Applied Physics*, vol. 44(4B), 2005, pp. 2854-2859.
Sakata, T. et al., "DNA Sequencing Based on Intrinsic Molecular Charges", *Angewandte Chemie International Edition 2006*, vol. 118, 2006, pp. 2283-2286.
Sakata, T. et al., "DNA Sequencing Based on Intrinsic Molecular Charges", *Angewandte Chemie International Edition 2006*, vol. 45, 2006, pp. 2225-2228.
Sakata, T. et al., "DNA Sequencing Using Genetic Field Effect Transistor", *13th Intl. Conf. on Solid-State Sensors, Actuators and Microsystems*, Jun. 5-9, 2005, Seoul, Korea, 2005.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005, Tokyo, Japan*, 2005 Intl Microprocesses and Nanotech Conf., Hotel Bellclassic, 2005, pp. 42-43.
Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of DNA Using Genetic Transistor", *Denki Gakkai Kenkyukai Shiryo Chemical Sensor Kenkyukai*, CHS-03-51-55, 2003, pp. 1-5.
Sakata, T. et al., "Potentiometric Detection of Single Nucleotide Polymorphism by Using a Genetic Field-effect transistor", *ChemBioChem*, vol. 6, 2005, pp. 703-710.

Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, pp. 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, R. et al., "A new approach to immunoFET operation", *Biosensors & Bioelectronics*, vol. 5, 1990, pp. 103-124.
Schasfoort, R. et al., "Field-effect flow control for microfabricated fluidic networks", *Science*, vol. 286(5441), 1999, pp. 942-945.
Schoning, M. et al., "bio FEDs (Field-Effect Devices): State-of-the-Art and New Directions", *Electroanalysis*, vol. 18(19-20), 2006, 1893-1900.
SG200903992-6 Search and Examination Report Mailed Jan. 20, 2011.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", *IEEE Trans Circuits Syst—I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, pp. 5354-5361.
Simonian, A. L. et al., "FET based biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Starodub, N. et al., "Immunosensor for the determination of the herbicide simazine based on an ion-selective field-effect transistor", *Analytica Chimica Acta*, vol. 424, 2000, pp. 37-43.
Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.
Tomaszewski, D. et al., "Electrical characterization of ISFETs", *J Telecomm Info Technol*, Mar. 2007, pp. 55-60.
Toumazou, C. et al., "Using transistors to linearase biochemistry", *Electronics Letters*, vol.43(2), Jan. 18, 2007, 3 pages.
Truman, P., "Monitoring liquid transport and chemical composition in lab on . . . ", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, J. et al., "ISFET Responses on a stepwise change in electrolyte concentration at constant pH", *Sensors Actuators B: Chemical*, vol. 18-19, 1994, pp. 56-59.
Van Kerkhof, J. et al., "The ISFET based heparin sensor with a monolayer of protamine as affinity ligand", *Biosensors & Bioelectronics*, vol. 10(3), 1995, pp. 269-282.
Van Kerkhof, J., "The Development of an ISFET-based Heparin Sensor", *Thesis*, 1994.

(56) References Cited

OTHER PUBLICATIONS

Wagner, T et al., "'All-in-one' solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad. of Sciences (PNAS)*, vol. 102(9), 2005, pp. 3208-3212.

Woias, P. et al., "Slow pH response effects of silicon nitride ISFET sensors", *Sensors and Actuators B*, vol. 48, 1998, pp. 501-504.

Woias, P., "Modelling the short time response of ISFET sensors", *Sensors and Actuators B*, vol. 24-25, 1995, pp. 211-217.

Wu, P. et al., "DNA and protein microarray printing on silicon nitride waveguide surfaces", *Biosensens Bioelectron*, vol. 21(7), 2006, pp. 1252-1263.

Xu, J-J et al., "Analytical Aspects of FET-Based Biosensors", *Frontiers in Bioscience*, vol. 10, 2005, pp. 420-430.

Yeow, T.C.W. et al., "A very large integrated pH-ISFET sensor array chip compatible with standard CMOS processes", *Sensor and Actuators B*, vol. 44, 1997, pp. 434-440.

Yuqing, M. et al., "Ion sensitive field effect transducer-based biosensors", *Biotechnology Advances*, vol. 21, 2003, pp. 527-534.

Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

\* cited by examiner

METHODS AND SYSTEMS FOR POINT OF USE REMOVAL OF SACRIFICIAL MATERIAL

FIELD

This application generally relates to methods and systems for nucleic acid sequencing. More specifically, the specification relates to methods and systems for processing and/or analyzing nucleic acid sequencing data and/or signals.

BACKGROUND

Deoxyribonucleic acid, or DNA, is the genetic material in the nuclei of all cells. DNA is made of chemical building blocks called nucleotides. Nucleotides comprise three parts: a phosphate group, a sugar group and one of four types of nitrogen bases. The four types of nitrogen bases found in nucleotides are: adenine (A), thymine (T), cytosine (C) and guanine (G). To form a strand of DNA, nucleotides are linked into chains, with the phosphate and sugar groups alternating.

The structure of a DNA molecule was first described in 1953 by Francis Crick and James D. Watson as two strands wound around each other in a double helix to resemble a twisted ladder. The two strands of DNA contain complementary information: A forms hydrogen bonds only with T, C only with G. The precise order in which the four types of nitrogen bases (A, T, C, G) appear in the strand determines genetic characteristics of all life forms. The process of determining the precise order of nucleotides within a DNA molecule is termed DNA sequencing. DNA sequencing may be used to determine the sequence of individual genes, larger genetic regions (i.e. clusters of genes or operons), full chromosomes or entire genomes. Depending on the methods used, sequencing may provide the order of nucleotides in DNA or RNA isolated from cells of animals, plants, bacteria, archaea, or virtually any other source of genetic information. The resulting sequences may be used by researchers in molecular biology or genetics to further scientific progress or may be used by medical personnel to make treatment decisions.

Conventional methods of DNA sequencing comprise chemical (i.e. electrophoresis), optical, and electronic methods. As compared to other methods for detecting a DNA sequence, electronic sequencing methods differ from other sequencing technologies in that modified/labeled nucleotides and/or optics/optical measurements are not necessary. Instead, electronic sequencing methods rely on ion or other reaction byproducts to identify the relevant DNA sequence.

A type of electronic DNA sequencing, ion semiconductor sequencing is a method of DNA sequencing based on the detection of ions (for example, hydrogen ions) that are released during the polymerization of DNA. Ion semiconductor sequencing is a method of "sequencing by synthesis," during which a complementary strand is built by incorporation (pairing of bases) based on the sequence of a template strand.

The incorporation of a deoxyribonucleotide triphosphate (dNTP) into a growing DNA strand involves the formation of a covalent bond and the release of pyrophosphate and a positively charged hydrogen ion. A dNTP will only be incorporated if it is complementary to the leading unpaired template nucleotide. Ion semiconductor sequencing leverages this process by detecting whether a hydrogen ion is released when a single species of dNTP is provided to the reaction.

Hydrogen ions may be detected by providing an array of microwells on a semiconductor chip. Beneath the layer of microwells is an ion sensitive layer, below which is an ion sensitive (ISFET) or a chemical sensitive (chemFET) sensor. Each microwell on the chip may contain a template DNA molecule to be sequenced. Each microwell containing a template strand DNA molecule also contains a DNA polymerase. A DNA polymerase is a cellular or viral enzyme that synthesizes DNA molecules from their nucleotide building blocks. A microfluidics device may be used to introduce a solution of unmodified A, T, C, or G dNTP into the microwells one after the other and one at a time. If an introduced dNTP is complementary to the next unpaired nucleotide on the template strand, a biochemical reaction occurs (which includes the release of a hydrogen ion) and the introduced dNTP is incorporated into the growing complementary strand by the DNA polymerase. If the introduced dNTP is not complementary there is no incorporation and no biochemical reaction. The release of a hydrogen ion during incorporation causes a change in the pH of the solution in the microwell. That change in the pH of the solution can be detected/measured by the ISFET or chemFET sensor and translated into an electrical pulse.

Before the next cycle of dNTP is introduced into the microwells, the microwells are flushed with a wash solution. Unattached dNTP molecules are washed out during the flush cycle. The detected series of electrical pulses are transmitted from the chip to a computer and are translated into a DNA sequence. Because nucleotide incorporation events are measured directly by electronics, intermediate signal conversion is not required. Signal processing and DNA assembly can then be carried out in software.

The chip may be fabricated by taking advantage of conventional semiconductor technology. However, the release of a hydrogen ion produces a small and transient signal that is difficult to measure. To further complicate detection and nucleic acid sequencing, ion detection is sensitive to various forms of contaminants on the chip surfaces. Accordingly, problems arise during manufacturing, packaging and exposure of the chip surfaces to the environment. Thus, there is a need for improved methods and an apparatus to prevent contamination of the chip surfaces for reliable ion detection and sequencing.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

SUMMARY

Figure 1:
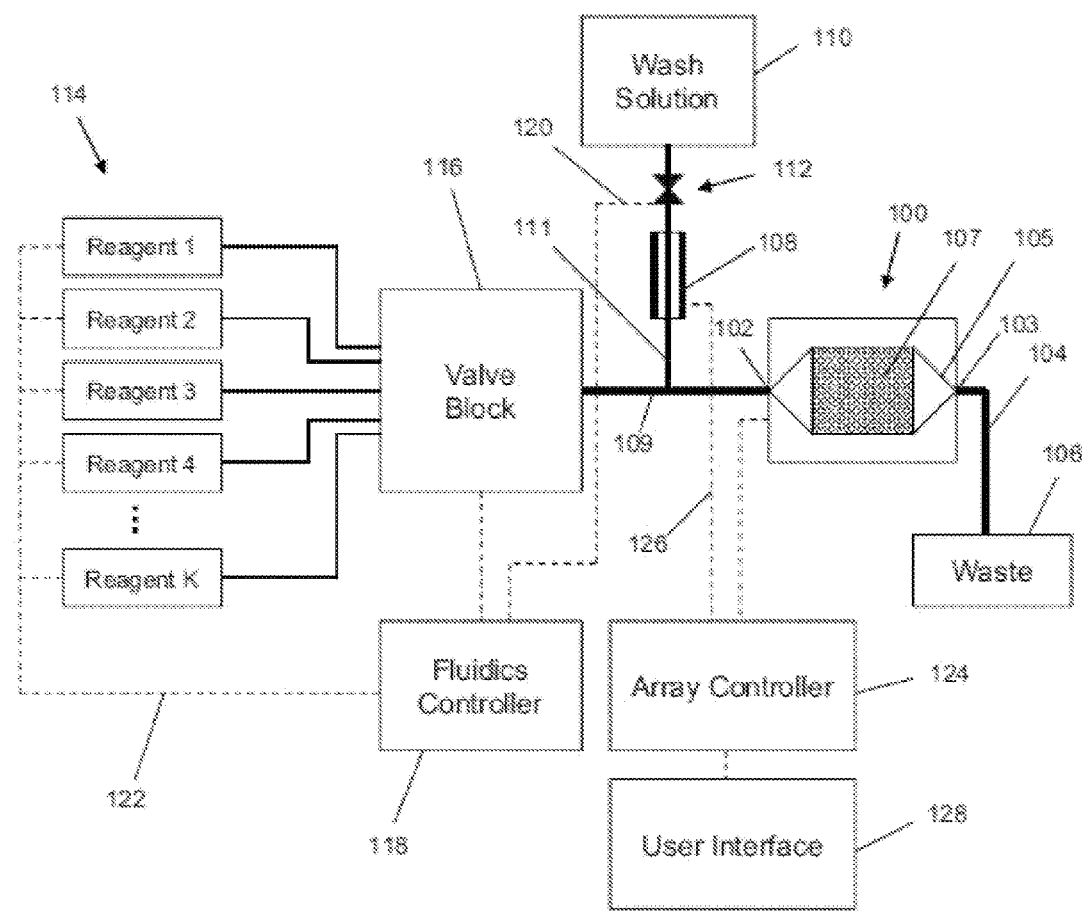
FIG. 1 illustrates components of a system for nucleic acid sequencing according to an exemplary embodiment.

The disclosure relates to methods of manufacturing a sensor for nucleic acid sequencing having a protective layer that prevents surface contamination of the sensor during various stages of fabrication. The disclosure further relates to a sensor for nucleic acid sequencing comprising an array of chemically-sensitive field effect transistors (chemFETs) and a conformal protective layer over the sensing surfaces, sidewalls of the cavities, and top surface of the array of chemFETs. The protective layer over the array of chemFETs may be removed by an end user before Nucleic acid sequencing is performed.

In one embodiment, the disclosure relates to a method of manufacturing a sensor for Nucleic acid sequencing. The method comprises forming an array of chemically-sensitive field effect transistors (chemFETs); depositing a dielectric layer over the chemFETs in the array; depositing a protective layer over the dielectric layer; etching the dielectric layer and the protective layer to form cavities corresponding to sensing surfaces of the chemFETs; and removing the protective layer. In another embodiment, the step of etching includes etching the dielectric layer and the protective layer together to form cavities corresponding to sensing surfaces of the chemFETs. In one embodiment, the protective layer is at least one of a polymer, photoresist material, noble metal, copper oxide, and zinc oxide. In another embodiment, the protective layer is removed using at least one of an acid, a base, and an oxidizing solution. For example, the protective layer may be removed using at least one of sodium hydroxide, organic solvent, aqua regia, ammonium carbonate, hydrochloric acid, acetic acid, and phosphoric acid. In another embodiment, the dielectric layer includes at least one of silicon oxide, silicon nitride and silicon oxynitride. In one embodiment, the method further comprises patterning a photosensitive etch mask and wherein the etching of the dielectric layer and the protective layer is a photolithographic process.

In another embodiment, the disclosure relates to a sensor for Nucleic acid sequencing. The sensor comprises an array of chemically-sensitive field effect transistors (chemFETs), each chemFET in the array having a floating gate structure including an upper surface; a dielectric layer over the upper surfaces of the floating gate structures of the chemFETs in the array, the dielectric layer including cavities extending to the upper surfaces of the floating gate structures and corresponding to sensing surfaces of the chemFETs; a conformal protective layer over the sensing surfaces, sidewalls of the cavities, and top surface of the array. In one embodiment, the protective layer defines a removable layer. In another embodiment, the protective layer is at least one of a polymer, photoresist, noble metal, copper oxide, and zinc oxide. In another embodiment, the protective layer is removed using at least one of sodium hydroxide, organic solvent, aqua regia, ammonium carbonate, hydrochloric acid, acetic acid, and phosphoric. In another embodiment, the dielectric layer includes at least one of silicon oxide, silicon nitride and silicon oxynitride. In another embodiment, the sensing material includes at least one of tantalum oxide, titanium oxide, and titanium nitride. In another embodiment, the sensing material is a metal oxide or metal nitride selected from one or more of the group of Al2O3, Ta2O5, HfO3, WO3, ZrO2, TiO2 or mixtures thereof.

DETAILED DESCRIPTION

FIG. 1 illustrates components of a system for nucleic acid sequencing according to an exemplary embodiment. The components include a flow cell and sensor array 100, a reference electrode 108, a plurality of reagents 114, valve block 116, wash solution 110, valve 112, fluidics controller 118, lines 120/122/126, passages 104/109/111, waste container 106, array controller 124, and user interface 128. The flow cell and sensor array 100 includes inlet 102, outlet 103, microwell array 107, and flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100.

Fluidics controller 118 may control driving forces for reagents 114 and the operation of valve 112 and valve block 116 with suitable software. Microwell array 107 may include an array of defined spaces or reaction confinement regions, such as microwells, for example, that is operationally associated with a sensor array 100 so that, for example, each microwell has a sensor suitable for detecting an analyte or reaction property of interest. Microwell array 107 may preferably be integrated with the sensor array as a single device or chip. The flow cell may have a variety of designs for controlling the path and flow rate of reagents over microwell array 107, and may be a microfluidics device. Array controller 124 may provide bias voltages and timing and control signals to the sensor, and collect and/or process output signals. User interface 128 may display information from the flow cell and sensor array 100 as well as instrument settings and controls, and allow a user to enter or set instrument settings and controls.

In an exemplary embodiment, such a system may deliver reagents to the flow cell and sensor array in a predetermined sequence, for predetermined durations, at predetermined flow rates, and may measure physical and/or chemical parameters providing information about the status of one or more reactions taking place in defined spaces or reaction confinement regions, such as, for example, microwells (or in the case of empty microwells, information about the physical and/or chemical environment therein). In an exemplary embodiment, the system may also control a temperature of the flow cell and sensor array so that reactions take place and measurements are made at a known, and preferably, a predetermined temperature.

In an exemplary embodiment, such a system may be configured to let a single fluid or reagent contact reference electrode 108 throughout an entire multi-step reaction. Valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between reference electrode 108 and the junction between passages 109 and 111 may be selected so that little or no amount of the reagents flowing in passage 109 and possibly diffusing into passage 111 reach the reference electrode 108. In an exemplary embodiment, wash solution 110 may be selected as being in continuous contact with the reference electrode 108, which may be especially useful for multi-step reactions using frequent wash steps.

Figure 2:
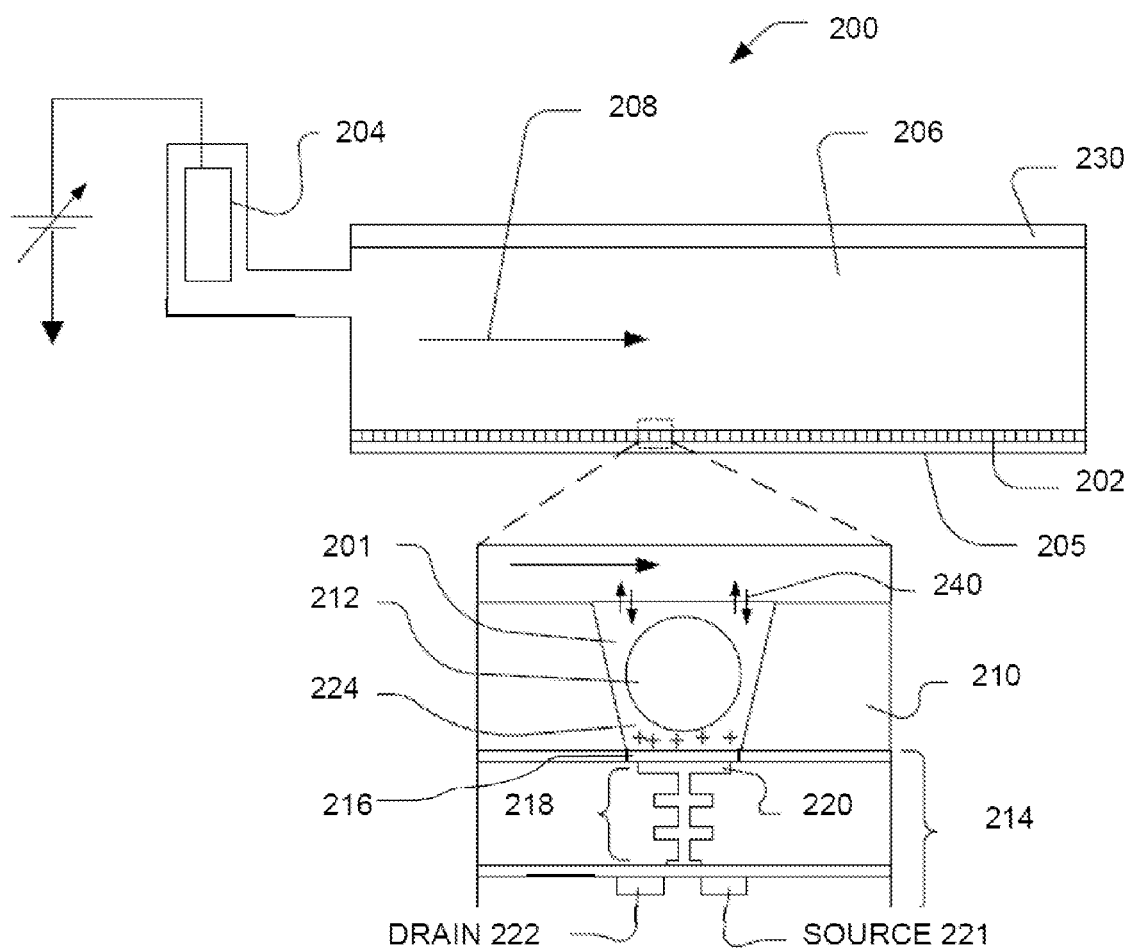
FIG. 2 illustrates cross-sectional and expanded views of a flow cell for nucleic acid sequencing according to an exemplary embodiment.

FIG. 2 is an illustration of expanded and cross-sectional views of an exemplary flow cell 200 and shows a portion of an exemplary flow chamber 206. A reagent flow 208 flows across a surface of a microwell array 202, in which reagent flow 208 flows over the open ends of the microwells. Microwell array 202 and sensor array 205 together can form an integrated unit forming a bottom wall (or floor) of flow cell 200. Reference electrode 204 can be fluidly coupled to flow chamber 206. Further, flow cell cover 230 encapsulates flow chamber 206 to contain reagent flow 208 within a confined region.

Example flow cell structures and associated components can be found in U.S. Pat. No. 7,948,015 (filed Dec. 14, 2007).

FIG. 2 also illustrates an expanded view of exemplary microwell 201, dielectric layer 210, and exemplary sensor 214. The volume, shape, aspect ratio (such as base width-to-well depth ratio), and other dimensional characteristics of the microwells are design parameters that depend on a particular application, including the nature of the reaction taking place, as well as the reagents, byproducts, and labeling techniques (if any) that are employed. Sensor 214 can be an ion-sensitive field-effect transistor (ISFET) with a floating gate structure 218 having sensor plate 220 separated from the microwell interior by ion-sensing layer 216. Ion-sensing layer 216 may cover the entire microwell or a portion thereof. Ion-sensing layer 216 may cover surfaces between microwells. (See, for example, FIGS. 6A-B). Ion-sensing layer 216 may be a metal oxide layer such as, for example and without limitation, silicon nitride, tantalum oxide, aluminum oxide, or a combination thereof.

Ion-sensing layer 216, particularly in a region above floating gate structure 218 and sensor plate 220, can alter the electrical characteristics of the ISFET so as to modulate a current flowing through a conduction channel of the ISFET. That is, sensor 214 can be responsive to (and generate an output signal related to) the amount of charge 224 present on ion-sensing layer 216 opposite of sensor plate 220. Changes in charge 224 can cause changes in a current between source 221 and drain 222 of the ISFET. In turn, the ISFET can be used to provide a current-based output signal or indirectly with additional circuitry to provide a voltage-based output signal. Reactants, wash solutions, and other reagents can move in and out of the microwells by a diffusion mechanism 240.

In an embodiment, reactions carried out in microwell 201 can be analytical reactions to identify or determine characteristics or properties of an analyte of interest. Such reactions can generate directly or indirectly byproducts that affect the amount of charge adjacent to sensor plate 220. If such byproducts are produced in small amounts or rapidly decay or react with other constituents, then multiple copies of the same analyte can be analyzed in microwell 201 at the same time in order to increase the output signal ultimately generated. For instance, multiple copies of an analyte may be attached to solid phase support 212, either before or after deposition into a microwell. The solid phase support 212 may be a microparticle, nanoparticle, bead, or the like. For nucleic acid analyte, multiple, connected copies may be made by rolling circle amplification (RCA), exponential RCA, and other similar techniques, to produce an amplicon without the need of a solid support.

FIGS. 3A-F are schematic representations of a method of manufacturing a sensor with a protective layer according to one embodiment. Sensor 314 may be an ion sensitive (ISFET) or a chemical sensitive (chemFET) sensor with a floating gate 318 having sensor plate 320 separated from the microwell interior by an ion-sensing layer (not shown), and may be predominantly responsive to (and generate an output signal related to) an amount of charge present on the ion-sensing layer opposite of sensor plate 320. Changes in the amount of charge cause changes in the current between source 321 and drain 322 of sensor 314, which may be used directly to provide a current-based output signal or indirectly with additional circuitry to provide a voltage output signal.

Figure 3A:
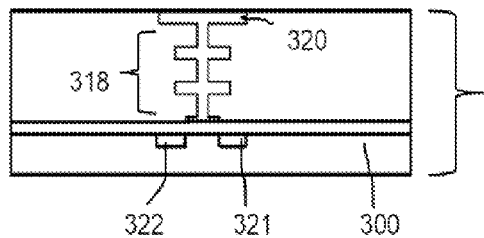
FIGS. 3A-F are schematic representations of a method of manufacturing a sensor with a protective layer according to an exemplary embodiment.

FIG. 3A shows a sensor 314 which may be an ion sensitive (ISFET) or a chemical sensitive (chemFET). Substrate 300 may comprise a silicon wafer, or other relevant materials for CMOS fabrication as appropriate.

Figure 3B:
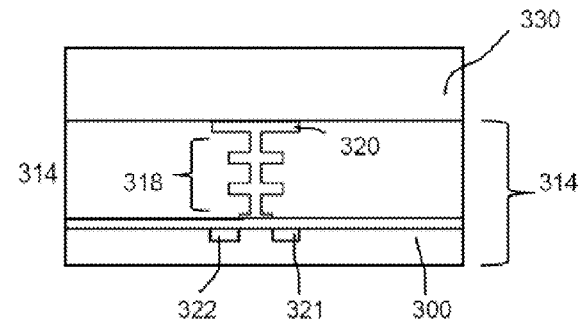

FIG. 3B shows dielectric layer 330 disposed on sensor 314. Dielectric layer 330 may comprise silicon oxide, silicon nitride and silicon oxynitride.

Figure 3C:
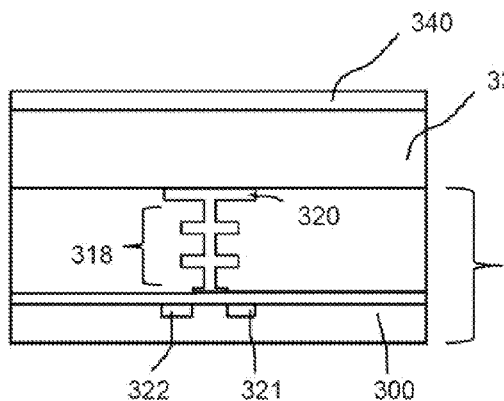

FIG. 3C shows protective layer 340 disposed on dielectric layer 330. Protective layer 340 may comprise a polymer, photoresist material, noble metal, copper oxide, or zinc oxide.

Figure 3D:
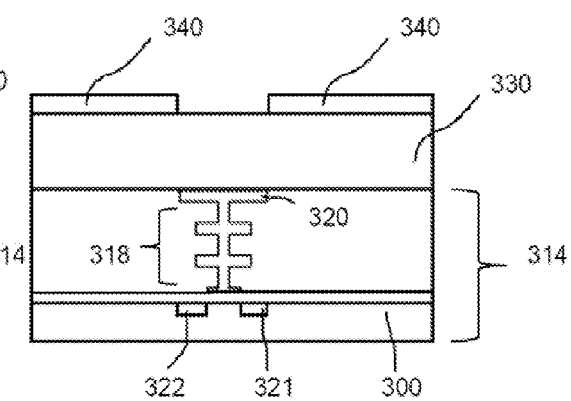

FIG. 3D shows sensor 314 after patterning of protective layer 340.

Figure 3E:
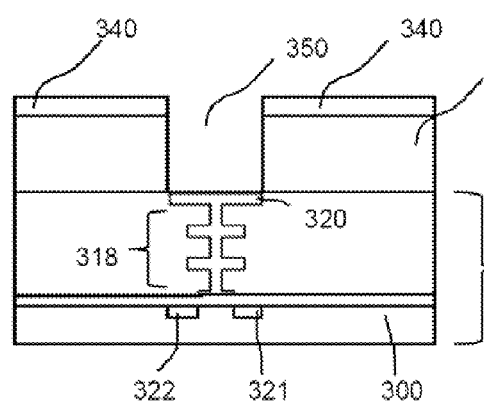

FIG. 3E shows cavity 350 extending to the upper surfaces of the floating gate structures and corresponding to sensing surfaces of the chemFETs after etching protective layer 340 and dielectric layer 330.

Figure 3F:
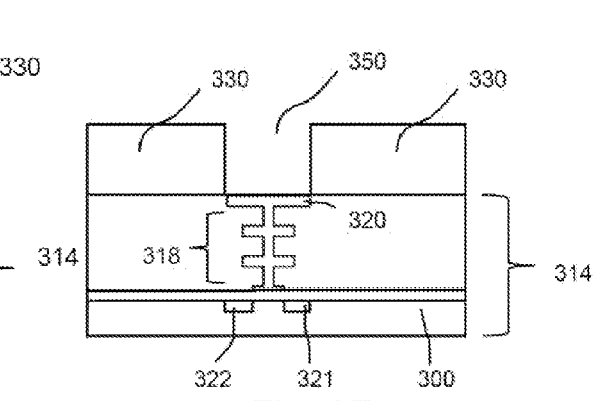

FIG. 3F shows sensor 314 with cavity 350 after removal of protective layer 340. Protective layer 340 may be removed using sodium hydroxide, organic solvent, aqua regia, ammonium carbonate, hydrochloric acid, acetic acid, and phosphoric acid, for example.

Figure 4A:
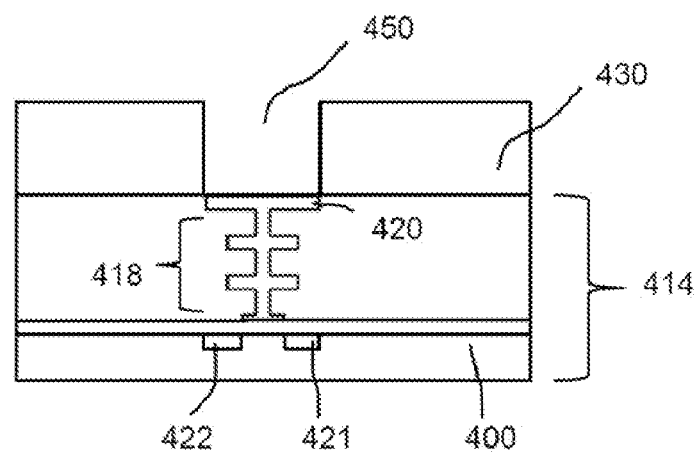
FIGS. 4A-C are schematic representations of a sensor with a protective layer according to an exemplary embodiment.
Figure 4B:
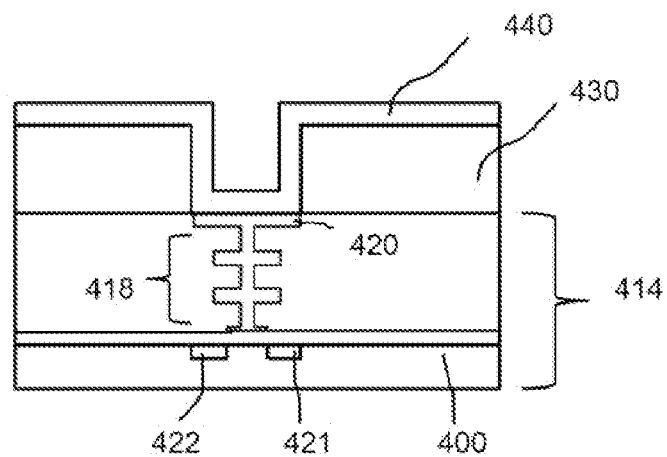
Figure 4C:
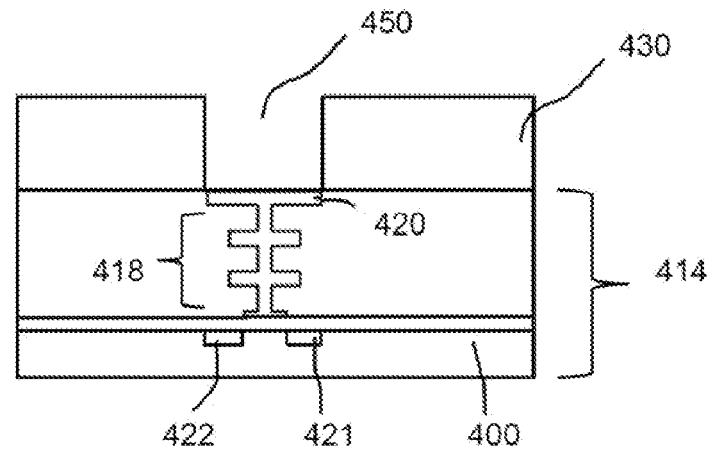

FIGS. 4A-C are schematic representations of a sensor with protective layer 440 according to one embodiment. Sensor 414 may be an ion sensitive (ISFET) or a chemical sensitive (chemFET) sensor 414 with floating gate 418 having sensor plate 420 separated from the microwell interior by an ion-sensing layer (not shown, see FIGS. 6A and 6B for example), and may be predominantly responsive to (and generate an output signal related to) an amount of charge present on the ion-sensing layer opposite of sensor plate 420. Changes in the amount of charge cause changes in the current between source 421 and drain 422 of sensor 414, which may be used directly to provide a current-based output signal or indirectly with additional circuitry to provide a voltage output signal.

FIG. 4A shows sensor 414 with cavity 450 formed for use as a microwell, for example, as described above with reference to FIG. 1. Dielectric layer 430 extends to the upper surface of the floating gate structure. Dielectric layer 430 may include at least one of silicon oxide, silicon nitride and silicon oxynitride. Substrate 400 may comprise a silicon wafer, or other relevant materials for CMOS fabrication as appropriate.

FIG. 4B shows a conformal protective layer 440 over the microwell structure of sensor 414. Protective layer 440 may comprise a polymer, photoresist material, noble metal, copper oxide, or zinc oxide.

FIG. 4C shows sensor 414 with cavity 450 formed for use as a microwell after removal of protective layer 440. Protective layer 440 serves to protect sensor 414 from environmental contamination and is removed before performing nucleic acid sequencing according to an exemplary embodiment. Protective layer 440 may be removed using at least one of sodium hydroxide, organic solvent, aqua regia, ammonium carbonate, hydrochloric acid, acetic acid, or phosphoric acid.

Figure 5:
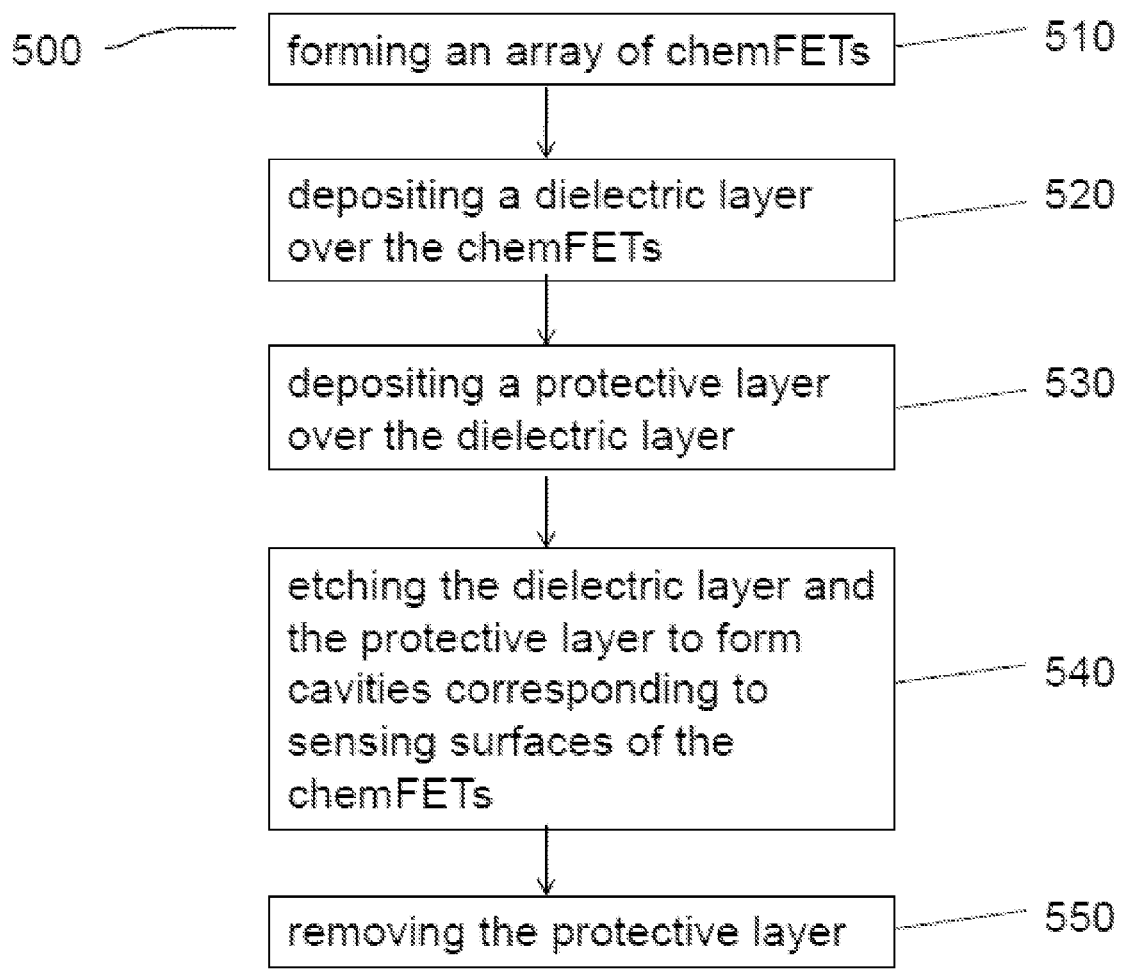
FIG. 5 is flow diagram for performing a method of manufacturing a sensor with a protective layer according to an exemplary embodiment.

FIG. 5 is flow diagram for performing a method of manufacturing a sensor with a protective layer 500 according to one embodiment. Step 510 includes forming an array of chemically-sensitive field effect transistors (chemFETs). Step 520 includes depositing a dielectric layer over the chemFETs in the array. Step 530 includes depositing a protective layer over the dielectric layer. Step 540 includes etching the dielectric layer and the protective layer to form cavities corresponding to sensing surfaces of the chemFETs. Step 550 includes removing the protective layer. The protective layer serves to protect the sensor from environmental contamination and is removed before performing nucleic acid sequencing according to an exemplary embodiment.

In one embodiment, the dielectric layer and the protective layer are etched together to form cavities corresponding to sensing surfaces of the chemFETs. In one embodiment, the protective layer comprises a polymer, photoresist material, noble metal, copper oxide, or zinc oxide. In one embodiment, the protective layer is removed using at least one of sodium hydroxide, organic solvent, aqua regia, ammonium carbonate, hydrochloric acid, acetic acid, or phosphoric acid. In one embodiment, the dielectric layer includes at least one of silicon oxide, silicon nitride and silicon oxynitride. In one embodiment, a further act includes patterning a photosensitive etch mask, wherein the etching of the dielectric layer and the protective layer is a photolithographic process. In one embodiment, the protective layer removal includes removal of photoresist residue contamination resulting from the etching step.

Figure 6A:
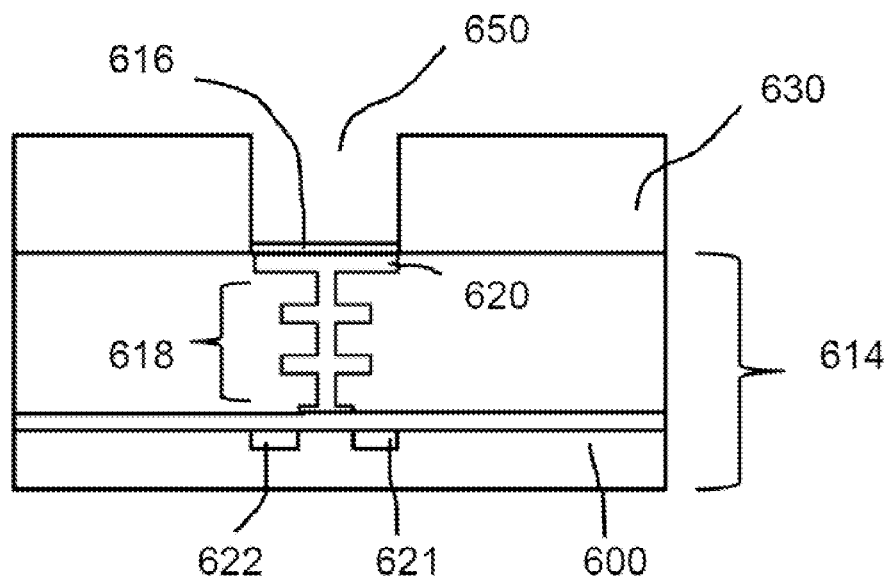
FIGS. 6A-B are schematic representations of a sensor with ion-sensing layers according to different exemplary embodiments.
Figure 6B:
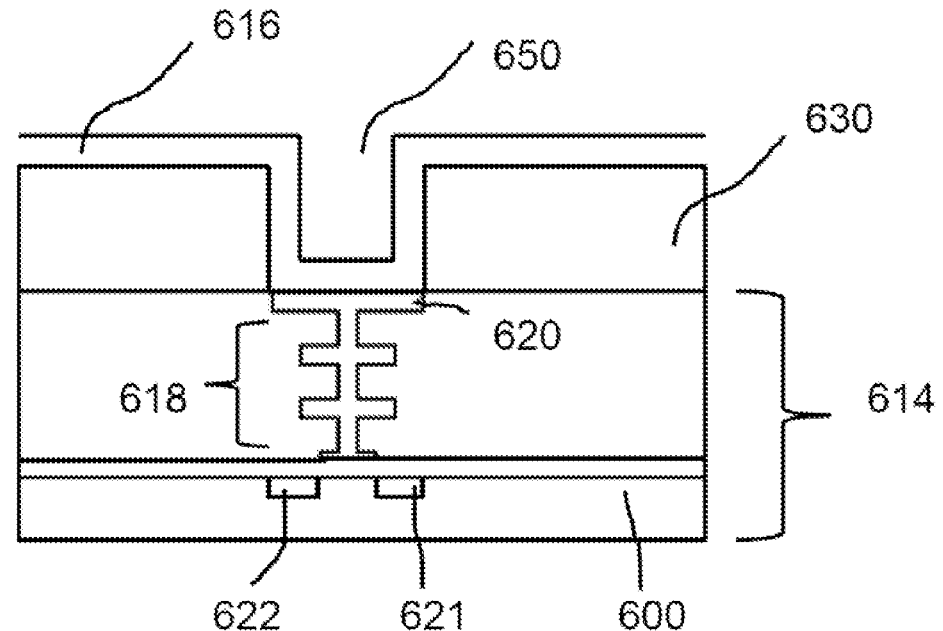

FIGS. 6A-B are schematic representations of exemplary sensors with cavity 650 formed for use as a microwell, for example, as described above with reference to FIG. 1. Sensor 614 may be an ion sensitive (ISFET) or a chemical sensitive (chemFET) sensor 614 with floating gate 618 having sensor plate 620 separated from the microwell interior by an ion-sensing layer 616, and may be predominantly responsive to (and generate an output signal related to) an amount of charge present on the ion-sensing layer opposite of sensor plate 620. Changes in the amount of charge cause changes in the current between source 621 and drain 622 of sensor 614, which may be used directly to provide a current-based output signal or indirectly with additional circuitry to provide a voltage output signal. Substrate 600 may comprise a silicon wafer, or other relevant materials for CMOS fabrication as appropriate.

The invention claimed is:

1. A sensor, comprising:
an array of chemically-sensitive field effect transistors (chemFETs), each chemFET in the array having a floating gate structure including an upper surface;
a dielectric layer over the upper surfaces of the floating gate structures of the chemFETs in the array, the dielectric layer including cavities extending to the upper surfaces of the floating gate structures and corresponding to sensing surfaces of the chemFETs;
a conformal protective layer over the sensing surfaces, sidewalls of the cavities, and top surface of the array.

2. The sensor of claim 1, wherein the protective layer defines a removable layer.

3. The sensor of claim 1, wherein the protective layer is at least one of a polymer, photoresist, noble metal, copper oxide, and zinc oxide.

4. The sensor of claim 1, wherein the protective layer is removed using at least one of sodium hydroxide, organic solvent, aqua regia, ammonium carbonate, hydrochloric acid, acetic acid, and phosphoric.

5. The sensor of claim 1, wherein the dielectric layer includes at least one of silicon oxide, silicon nitride and silicon oxynitride.

6. The sensor of claim 1, wherein the sensing surface comprises at least one of tantalum oxide, titanium oxide, and titanium nitride.

7. The sensor of claim 1, wherein the sensing surface comprises a metal oxide or metal nitride selected from one or more of the group of $Al_2O_3$, $Ta_2O_5$, $HfO_3$, $WO_3$, $ZrO_2$, $TiO_2$ or mixtures thereof.

* * * * *